United States Patent
Karlsson et al.

(10) Patent No.: US 7,591,168 B2
(45) Date of Patent: Sep. 22, 2009

(54) TEST EQUIPMENT SYSTEM AND METHOD FOR TESTING A COMPONENT

(75) Inventors: Kajsa Karlsson, Malmö (SE); Diana Sipöcz, Lund (SE)

(73) Assignee: Sony Ericsson Mobile Communications AB, Lund (SE)

( * ) Notice: Subject to any disclaimer, the term of this patent is extended or adjusted under 35 U.S.C. 154(b) by 42 days.

(21) Appl. No.: 11/738,970

(22) Filed: Apr. 23, 2007

(65) Prior Publication Data

US 2008/0184773 A1 Aug. 7, 2008

Related U.S. Application Data

(60) Provisional application No. 60/887,845, filed on Feb. 2, 2007.

(51) Int. Cl.
*G01N 3/307* (2006.01)
(52) U.S. Cl. .................................................. 73/12.09
(58) Field of Classification Search ................ 73/12.09, 73/12.13
See application file for complete search history.

(56) References Cited

U.S. PATENT DOCUMENTS

| | | | | |
|---|---|---|---|---|
| 4,034,603 | A * | 7/1977 | Leeb et al. ..................... 73/79 |
| 4,470,293 | A * | 9/1984 | Redmon ..................... 73/12.09 |
| 4,640,120 | A * | 2/1987 | Garritano et al. ........... 73/12.13 |
| 5,696,312 | A * | 12/1997 | Lee et al. ..................... 73/12.13 |
| 5,739,411 | A * | 4/1998 | Lee et al. ..................... 73/12.13 |
| 6,138,501 | A * | 10/2000 | Rastegar ......................... 73/82 |
| 6,508,103 | B1 * | 1/2003 | Shim et al. ................. 73/12.06 |
| 6,848,293 | B2 * | 2/2005 | DeRuiter et al. ........... 73/12.13 |
| 6,892,564 | B2 * | 5/2005 | Ishikawa ..................... 73/12.06 |
| 6,925,858 | B2 * | 8/2005 | Miles et al. ..................... 73/84 |
| 6,941,793 | B2 * | 9/2005 | Rioux ........................ 73/12.11 |
| 6,976,387 | B2 * | 12/2005 | Anthe et al. ..................... 73/83 |
| 7,137,285 | B2 * | 11/2006 | Stroppiana ................. 73/12.13 |
| 7,367,214 | B2 * | 5/2008 | Goyal ......................... 73/12.09 |
| 7,430,892 | B2 * | 10/2008 | McNamara et al. ........ 73/12.13 |
| 2004/0261493 | A1 * | 12/2004 | Lee ............................. 73/12.09 |
| 2004/0261494 | A1 * | 12/2004 | Lee ............................. 73/12.09 |
| 2005/0016256 | A1 * | 1/2005 | Ishikawa ..................... 73/12.13 |
| 2005/0178184 | A1 * | 8/2005 | Stroppiana ................. 73/12.13 |
| 2008/0110237 | A1 * | 5/2008 | McNamara et al. ........ 73/12.13 |

FOREIGN PATENT DOCUMENTS

| | | |
|---|---|---|
| JP | 2000 249620 | 9/2000 |
| JP | 2005 062003 | 3/2005 |
| KR | 2002 0031442 | 5/2002 |

OTHER PUBLICATIONS

International Search Report and Written Opinion for corresponding Application No. PCT/EP2007/057567, mailed Nov. 22, 2007.

* cited by examiner

*Primary Examiner*—Lisa M Caputo
*Assistant Examiner*—Freddie Kirkland, III
(74) *Attorney, Agent, or Firm*—Renner, Otto, Boisselle & Sklar, LLP (57) ABSTRACT

A test equipment system and method for testing a component of an article wherein the system comprises a force element arranged to move from a first position to a second position, a striker element connected to the force element arranged at one end of the force element, a frame structure arranged to guide and support the force element between the two positions, the second end of the force element being connected to the frame structure, wherein the force element in the first position is in an energised state and the force element in the second position is arranged to impact the striker element against the component.

14 Claims, 12 Drawing Sheets

TEST EQUIPMENT SYSTEM AND METHOD FOR TESTING A COMPONENT

CROSS-REFERENCE TO RELATED APPLICATION

This application claims the benefit of U.S. Provisional Patent Application Ser. No. 60/887,845, filed Feb. 2, 2007, which is incorporated herein by reference in its entirety.

FIELD OF THE INVENTION

The invention relates to a test equipment system and a method of testing a component of an article. Specifically, the invention relates to a test equipment system and method of testing wherein the testing compensates the weight difference between the component and the article.

BACKGROUND OF THE INVENTION

In a constantly changing market, it is important to get your product out on the market as soon as possible. This is especially important for mobile phones since their life cycle is short. Products have drastically reduced their time to get on the market during the last few years. Nowadays the components are mainly developed through experience than testing and investigation. However, a number of tests are used today to test mobile phones. These test specifications are called GREAT, Global, Reliability and Environmental Test Specification and contain climate tests (high and low temperature, humidity, solar radiation etc), durability tests (repeated operation, fatigue), electrical tests (ESD, excessive voltage etc), functional tests (inspections, performance check, acoustical checks), mechanical tests (free fall, vibration, bend, pressure etc) and reliability tests (accelerated ageing). All these test are made on complete assembled phones and this is both time demanding and costly.

To develop a mobile phone it often requires a number of prototypes, generally four, before the phone is launched. Each prototype is GREAT tested and if one component is not durable enough, some changes have to be made and then the new component has to wait for the next prototype to be tested again. This may sometimes result in that it requires even more than four prototypes before the phone can be launched. A previous component impact tester comprising a pendulum was previously tested. The main problem with the pendulum was that it was a very large and ungainly design, about 2 meters high. Because of its size, it was not practical and not safe enough for the user. Another fundamental disadvantage was that the pendulum did not reach enough velocity when it hit the component.

Today a Free Fall test is a part of GREAT, which is used on mobile phones today. The purpose with the Free Fall test is to simulate the end user dropping the phone accidentally during intended use or during transport. There are three drop scenarios, face and/or edge and/or corner drops. All the drops are performed from 1.5 meters on a complete assembled mobile phone on concrete. The phone is powered on during the whole test. Nine tests are performed twice on each test phone and in total there are fifty-four tests made on 3 phones. The phone is inspected for damage and basic functionality after each test. All damages including cosmetic failure are reported by a template.

There is a need to find a precise testing of light moulded plastic parts before the mobile phone is completed in order to verify or control the strength of the plastic part.

There is further a need to find a test method that can point out variation in material quality in an earlier stage than the Free Fall test. Thereby, the material testing of the components can be moved out from the mobile manufacturer to the plastic component suppliers.

SUMMARY OF THE INVENTION

The invention relates to a system and a method for testing components of an article as stated in claims 1 and 11.

The invention relates to a test equipment system for testing a component of an article comprising:
- a force element arranged to move from a first position to a second position,
- a striker element connected to the force element arranged at one end of the force element,
- a frame structure arranged to guide and support the force element between the two positions, the second end of the force element being connected to the frame structure, wherein the force element in the first position is in an energised state and the force element in the second position is arranged to impact the striker element against the component.

The test equipment system may further comprise a component support arranged to support the component in an optional orientation and to place the component so that the striker impacts the component when the force element is in the second position.

The system may comprise a locking arrangement arranged to maintain the force element in the first position where the force element is in an energised state and wherein the locking arrangement is arranged to release the energy in the force element on command from a controller.

In an embodiment the locking arrangement may be a pneumatic arrangement comprising a compressed air source, a horizontal moving piston arranged to move perpendicular to the force direction of the force element and controlled by the compressed air source, a release arm connected to the piston, and a guiding house arranged to guide the release arm into the frame structure.

The locking arrangement may be at least one cotter.

The equipment may further comprise a tighter mechanism in order to position the force element in the first position.

Additionally, the tighter arrangement may be a screwing arrangement arranged to engage a lid arranged at the top of the frame and arranged to be tightened manually or by a machine.

In an embodiment the tighter arrangement is a pneumatic arrangement comprising a cylinder arranged to move in parallel to the force direction of the force element.

The force element may a spring element.

A lid may be arranged at the top of the frame structure.

The invention further relates to a method of testing a component of an article by using a test equipment system comprising a force element, a striker element connected to an end of the force element, a frame structure, and the second end of the force element is secured to the frame structure, comprising the steps of:
- moving the force element to the first position wherein the force element is energised;
- releasing the energy in the force element, and thereby impacting the striker element against the component.

The method may further comprise the step of:
- mounting the component in a component support so that the striker element impacts the component at a selected area of the component.

In addition, the method may further comprise the step of:
locking the force element in the first position after placing the force element in the first position.

The test equipment may further comprise a pneumatic arrangement comprising an compressed air source, a piston arranged to move perpendicular to the force direction of the force element and controlled by the compressed air source, a release arm connected to the piston, and a guiding house arranged to guide the release arm into the frame structure and a cylinder arranged to move parallel to the force direction of the force element, wherein the method further comprises the initial steps of:

positioning the force element in a third position lowering the striker element away from the component support just below a lid arranged at the frame structure; and mounting the component in a component support so that the striker element impacts the component at a selected area of the component.

Furthermore, the step of moving the force element may be performed by the release arm engaging the striker element and the cylinder forcing the force element to the selected first position by using compressed air from the compressed air source.

Additionally, the step of releasing the energy may be performed by withdrawing the release arm from the striker element using compressed air from the compressed air source.

The method may be controlled by an operator using buttons.

In an embodiment the method comprises the step of selecting a force of the force element for compensating the weight difference between the assembled article and the component.

The method may further comprise the steps of:
inspecting the component after the component has been impacted by the striker element; and
determining characteristics of the component by using information from the step of inspecting.

The method aims to provide a solution that has a great test range that takes into account that the impact test on one part, should correlate with the result on the same part in Free Fall test, in an assembled unit. The test objects are primarily moulded plastic, and components that weigh between 2 and 15 gram, and the test equipment in an embodiment should be able to handle impact from different directions and to adjust impact force.

This test equipment should further be easy to distribute to plastic suppliers, with minimal rigging and easy to use with a low risk of incorrect usage. The equipment may minimize complex calibration and be easy to maintain, with no or minimal risk for personal injuries during usage. The test equipment should further be available to a low price, which makes implementation fast and easy.

BRIEF DESCRIPTION OF THE DRAWINGS

The invention, together with further objectives and advantages thereof, may best be understood by reference to the following description taken in conjunction with the accompanying drawings in which.

DETAILED DESCRIPTION OF EMBODIMENTS OF THE INVENTION

There is a need to define, construct and verify a test method on component level that correlates with the Free Fall test on unit level. An embodiment of a test method and an embodiment of a system to perform the test are illustrated in the enclosed drawings. The illustrated embodiments are complements to the Free Fall test, which is the industry standard, and will focus on to test the material instead of testing the design of the assembled phone. Free fall tests are time consuming and expensive in that the whole assembled device is used and tested. The main purpose with the test equipment is to have a test method to control brittleness in an earlier stage than the Free Fall test that is to say already out at the plastic component suppliers to manufacturers. It will be possible to use the equipment during production to maintain the quality on the components.

The fundamental idea for the equipment is to compensate the weight loss, compared to a complete phone of a free fall test, with higher velocity on the strike.

In order to get an idea of what kind of velocity that needs to be used in a method wherein the mass is different of the test object than from the assembled device the following calculation was made.

The plastic components that are suppose to be tested, has a mass between 2-15 grams. In a Free Fall test an assembled phone, with a mass m of approximately 100 gram, is dropped from a height h of 1.5 m. The potential energy of this is $$W_p = mgh = 1.47 \text{ J} \quad (1)$$

The fundamental idea for the equipment is to compensate the weight loss, compared to a complete phone, with higher velocity on the strike. The kinetic energy is $$W_k = \frac{mv^2}{2} \quad (2)$$

No energy is lost, $$W_p = W_k \quad (3)$$

If all energy from a complete phone would be absorbed in one component with a mass of 2 g, a new velocity can be calculated.

$$v = \sqrt{\frac{2 \cdot W_p}{m}} = \sqrt{\frac{2 \cdot 1.47}{0.002}} = 38.4 \, m/s \qquad (4)$$

This is not a realistic assumption, but it is a worse-case scenario. It gives a vague idea of which velocities that the equipment should manage.

Figure 1A:
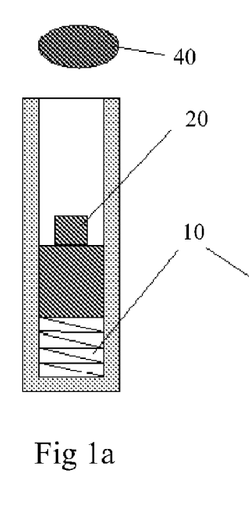
FIGS. 1*a*-1*c* shows an overview of a linear striker element.
Figure 1B:
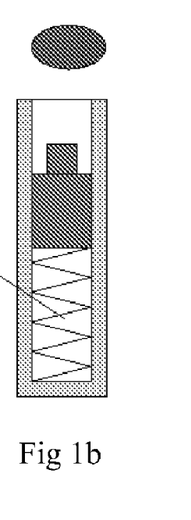
Figure 1C:
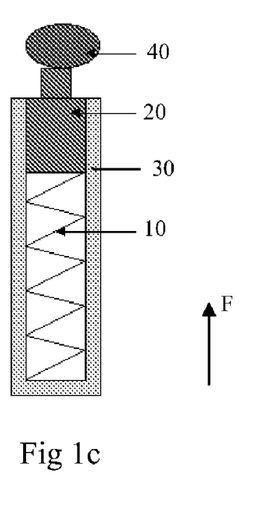

As shown in FIGS. 1a-1c, the equipment is built up around a force element such as a spring 10 that is compressed, released and the accomplished force will then be transformed to a striker 20 which will hit a component 40 to be tested. Hereinafter, embodiments of the equipment will be described. It should be understood that the force element may be any element that is able to affect a body placed in the travelling line of the force element. The force direction is indicated by the arrow in FIG. 1.

Figure 4:
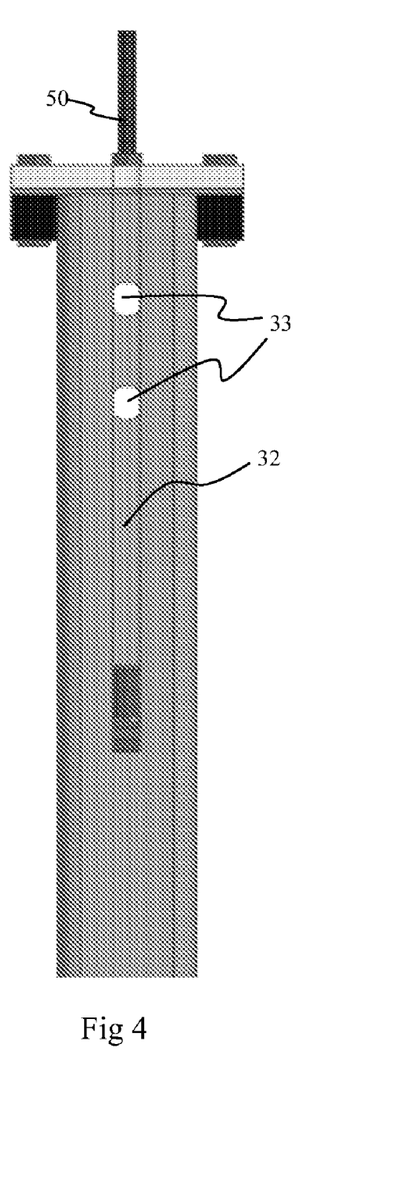
FIG. 4 shows an embodiment of a test equipment armed.

In an embodiment the spring 10 has a maximum force of F (532.5 N) and is placed inside a squared frame 30. Referring to FIG. 4, the frame 30 has a trace 32 along one side for the release arm. The frame 30 has also holes 33 on each side to prevent the air pressure that occurs during use. The frame 30 is made in cold-drawn steel. In an embodiment an extra frame 96 (see FIG. 12) is placed under the main one to get the correct height.

On top of the spring is a striker 20, which will hit the component 40. Referring to FIGS. 7a-7d, the striker 20 is designed to be as light as possible, it has a hollow inside 24 and round or square elevation 22 on top (may be in any shape). The material is POM. To have a hard hitting surface, a metallic layer, in this case a screw is placed on top (not shown).

Figure 12:
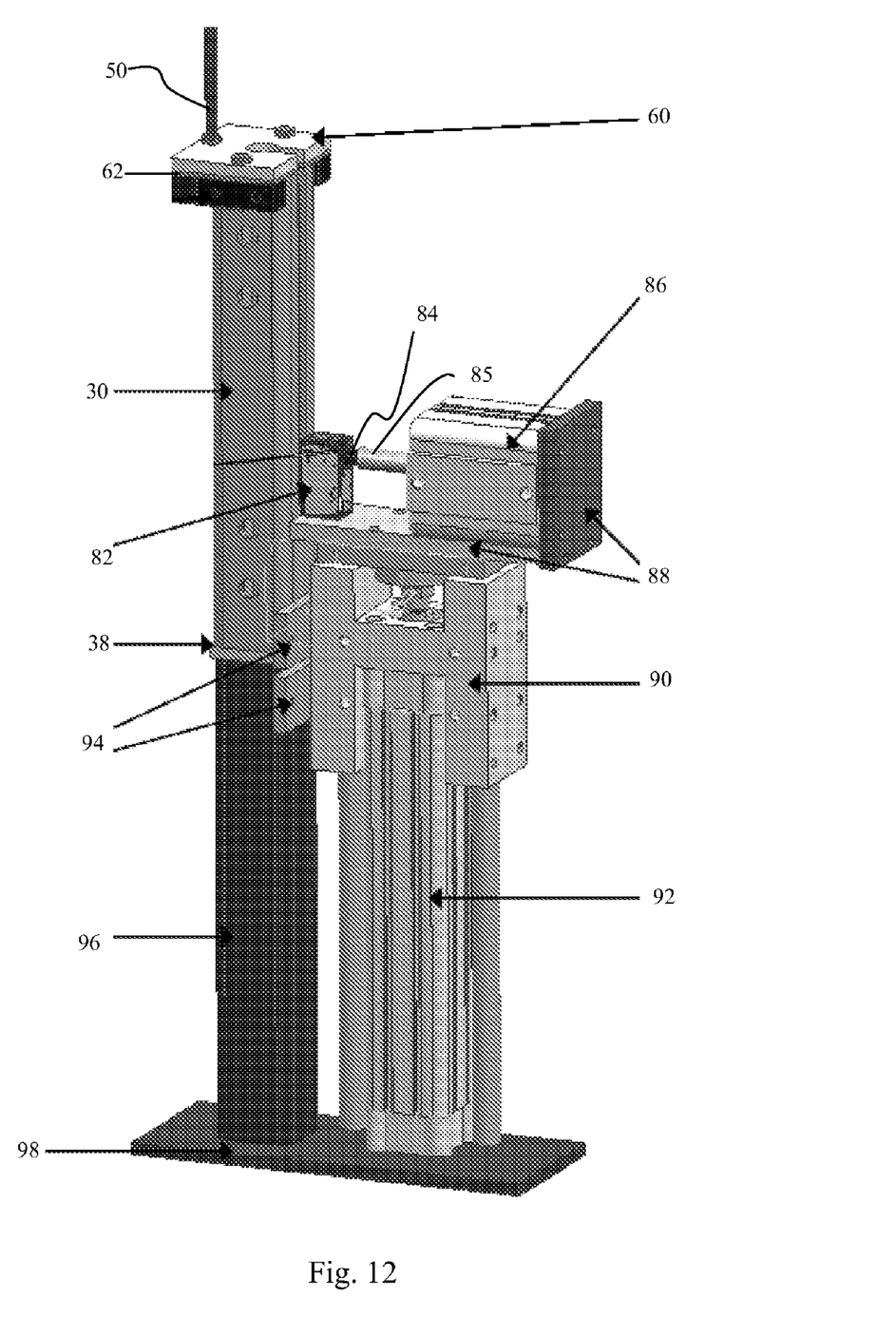
FIG. 12 shows an embodiment of the test equipment using pneumatics.
Figure 13:
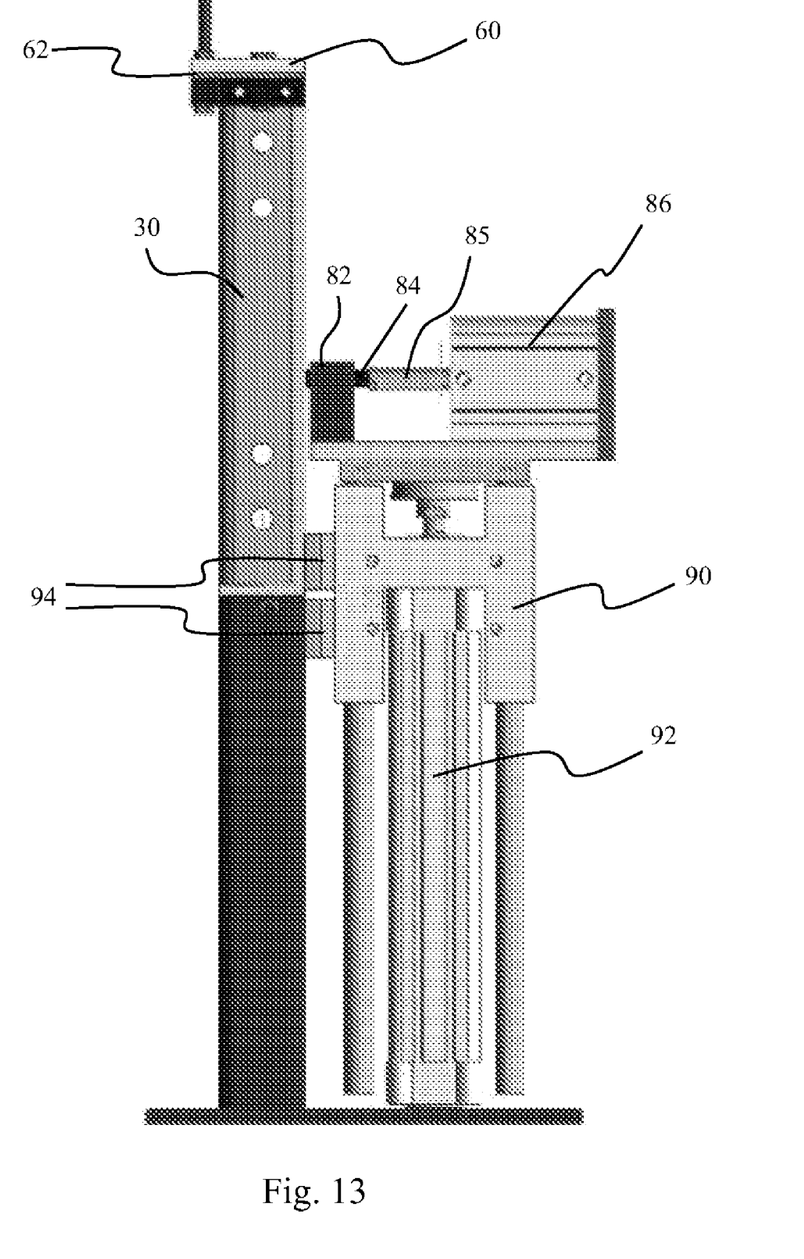
FIG. 13 shows a side view of the embodiment in FIG. 12.

In an embodiment shown in FIGS. 12 and 13 the tightening and releasing mechanism of the spring 10 is done with help of pneumatics, from FESTO. The large cylinder 92 (DNC-50-250-PPV-A) is tightening the spring and the small cylinder 86 (ADVU-63-50-P-A) will release it. The large cylinder 92 has a guide 90 (FENG-50-250-KF) to prevent the piston from bending. The small cylinder 86 has also a guide house 82, but it is own design. To connect the cylinders and to get the correct movements, a number of components are used, shown in FIG. 12. To connect the pneumatics to the frame 30, flanges 94 are used.

To keep the striker 20 inside the frame 30, a lid 60 is placed on top of the frame 30. To damp the hit, a layer 62 of rubber is arranged underneath the lid.

Figure 11:
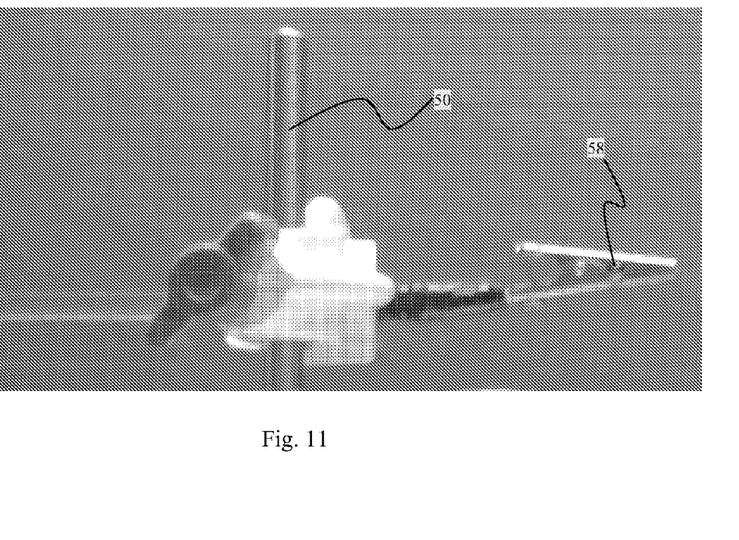
FIG. 11 shows an embodiment of a component support.

As shown in FIG. 11, a component support 50 may be a flexible arm of plastic with a clamp 58. It is assembled on the lid 60. The clamp 58 may be a crocodile clip.

Linear Striker

The illustrated Linear Striker is a design with a frame 30 and with a spring 10 within. The concept is illustrated in FIGS. 1a-1c. A tension spring or a pressure spring is a possible solution. A spring 10 can be chosen to enable the design to work in a wide range of velocities, this in order to function both with and without an added mass to a component 40. The velocity of the striker varies with the strikers distance to the component, which makes it possible to strike the components 40 with different forces. Depending on the components position, this type of design can be put in different positions, horizontal, with an angle or vertical.

Spring 10

Figure 2A:
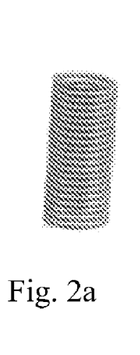
FIGS. 2*a*-2*b* shows a spring in an energised state and in a released state.
Figure 2B:
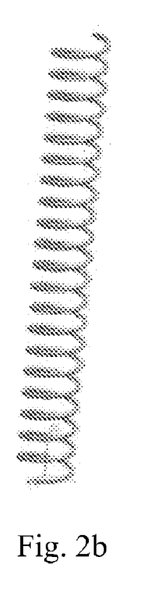

If a striker element 20 is centralized, a pressure spring 10 as a force element may be the best alternative. The spring 10 is an important part in the test equipment and calculations have been made to make sure that the chosen spring will manage to reach the required velocities. There are two important parameters that the spring energy depends on, the spring constant and the spring extension, they in their turn depend on each other. FIG. 2a shows a spring in an energised state, that is compressed, in a first position and FIG. 2b discloses a spring element in a second position wherein the spring element has released all the energy.

Figure 3:
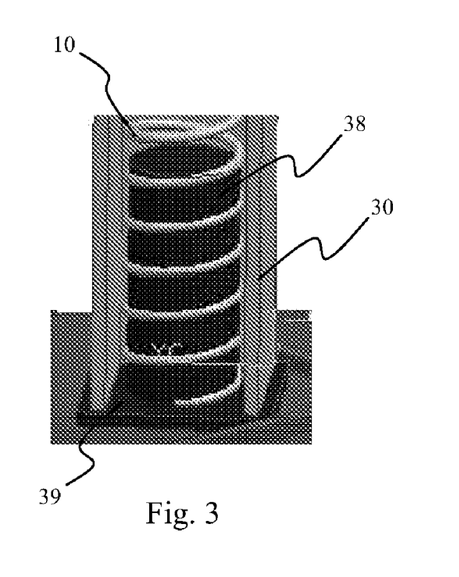
FIG. 3 shows an embodiment of a support structure for a spring according to an embodiment.

Referring to FIG. 3, to adjust different spring lengths to the frame 30, support parts 38 have been designed in steel. The selection of material is not very important, support parts 38 in plastic have also been made and they worked good as well. The reason to make them cylindrical is to fasten the spring roundabout with a cotter (not shown) that extends between the cylinder and the spring. The cotter is in its turn fastened in the frame. Two cylinders with different height were designed to suit each of the springs. The support part 38 is elongated from a ground plate 39 placed inside the frame 30.

Frame 30

Figure 5:
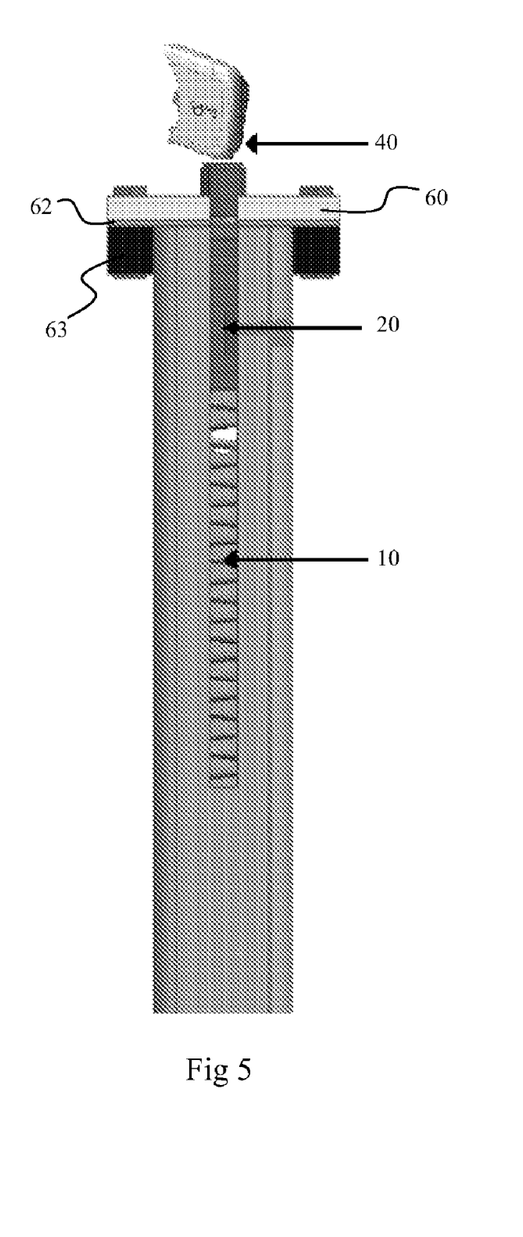
FIG. 5 shows an embodiment of a test equipment in a released state.
Figure 6A:
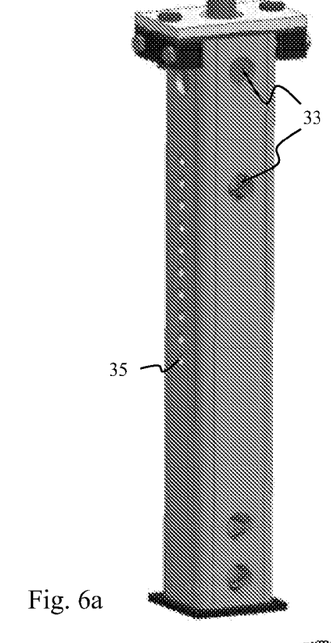
FIGS. 6*a*-6*c* show different embodiments of a frame of the test equipment.
Figure 6B:
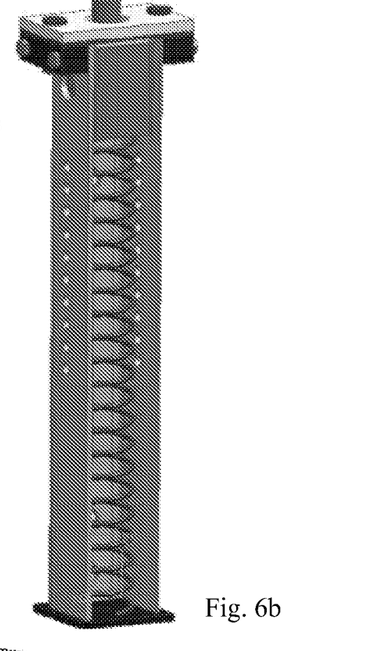
Figure 6C:
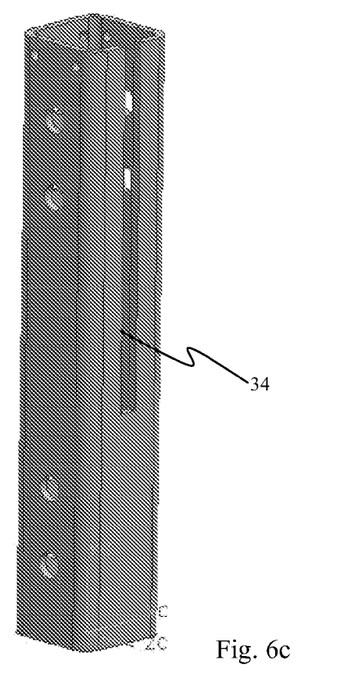

Referring to FIGS. 4 and 5, in order to support the spring 10 and striker 20 an elongated frame 30 is provided. The frame 30 may have any shaped cross section. A circular cross-section fits the spring 10 well, but with the squared cross-section it is easier to mount and place the striker 20 vertically. If the release function is attached on the frame 30 is it easier to fasten the release function on a squared cross-section. Different embodiments of the frame are shown in FIGS. 6a-6c.

In an embodiment of the invention the inner dimension has to be over 45 mm, including average diameter on the spring plus the wire thickness in order to fit the spring 10 inside the frame 30. To fit both a 4 and 5 millimeter wire thickness, a frame 30 with an outer dimension of 60×60 millimeters and wall thickness of 5 millimeters is suitable. A smooth surface on the inside minimizes the friction between the walls and the striker 20.

The height of the frame 30 depends on the length of the spring 10 together with the length on the striker 20. To be able to test different kind of springs in the same frame, the bottom of the frame may be adjustable. In an embodiment of the invention a specific length of the frame is decided.

The surface finish inside the frame may in an embodiment be blasted and lacquered in order to reduce the friction.

As shown in the illustrated embodiments in FIGS. 6a-6c, the frame 30 comprises a number of holes 33 arranged to relieve the built up air pressure inside the frame, that is, for the air to enter and exit on all the four sides on the frame both at the top and the bottom, thus, reducing the affect the built up pressure would have on the impact of the component 40. Furthermore, as shown in FIGS. 6a-6b the frame 30 comprises a number of locking holes 35, that is, holes arranged to be used with a cotter or the like locking the force element in different positions resulting in different impact velocities. In the illustrated frame 30 of FIG. 6c the frame 30 comprises a trace 34 suitable to be used in connection with a pneumatic tightening arrangement. As shown in FIG. 6b, the frame 30 may be U-shaped.

The trace may be provided at the side of the frame where a seam is placed, in that manner the friction between the striker and the seam should be avoided. The trace is made for the spring tightener to pass through. The trace is at the same time used as a variable adjustment of the velocity.

Striker Element 20

A squared section may be selected for the striker 20 to fit the frame 30 and the striker 20 should smoothly follow the inside of the frame 39 when the spring 10 is released from compressed state. However, any shape of the striker may be chosen. To avoid the effect of a drawer that can get stuck when it is not pulled out straight may the length of the striker be at least as long as it is wide. To get a good guiding of the striker, two points are put far away from each other.

As shown in FIGS. 7a-7d, the striker 20 is shaped so it can hit the component before it reaches the stand/lid 60. To do this a smaller squared/rounded part 22 is raised up from the rest of the striker 20. In the bottom of the strikers shown in FIGS. 7a-7c a circular protruding section is made to receive the spring 10. The main reason is to attach the section to the spring by a cotter. A light striker is preferred in that way the spring does not have to do too much work to lift the strikers mass. In an embodiment shown in FIG. 7d the striker may be in any light material such as a plastic material, POM, since it has low density compared to steel and comprise a hollowness 24 arranged to receive the spring. It may also have other good properties, such as good toughness, hardness, stiffness, high fatigue characteristic and good friction.

The top 22 of the striker may be alloyed with a hardened layer such as a screw to get a hard hit surface.

Figure 7A:
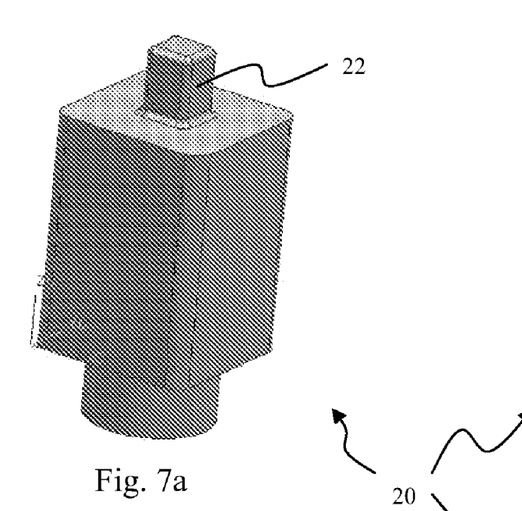
FIGS. 7*a*-7*d* show different embodiments of striker elements.
Figure 7B:
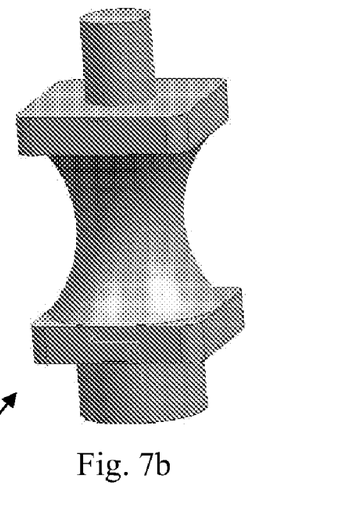
Figure 7C:
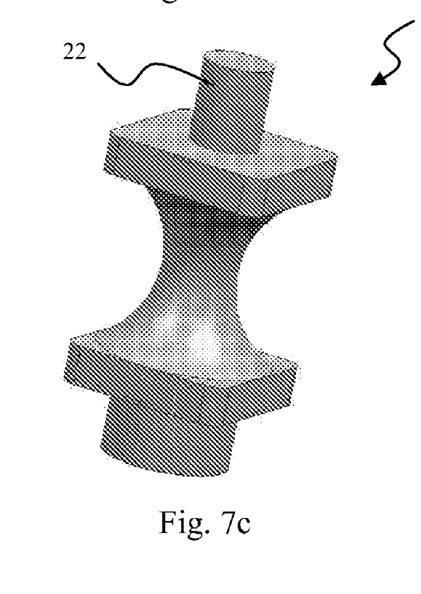
Figure 7D:
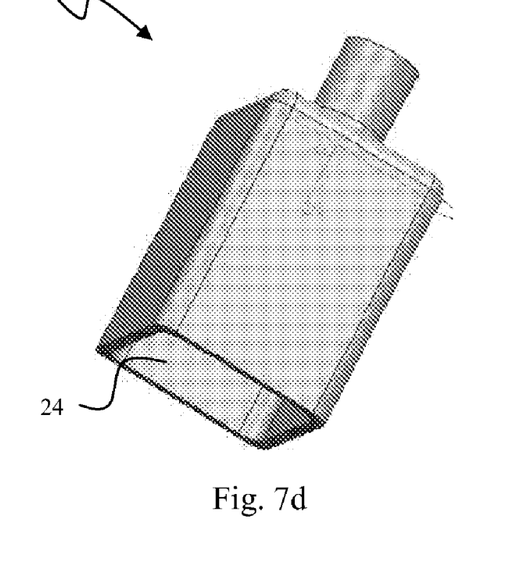

The striker may be constructed in a numerous of ways and shown in the accompanying FIGS. 7a-7d are just a few examples. The different embodiments of the striker have different weights, wherein FIG. 7d shows the lightest striker, a lighter striker results in a higher striker velocity.

Figure 8:
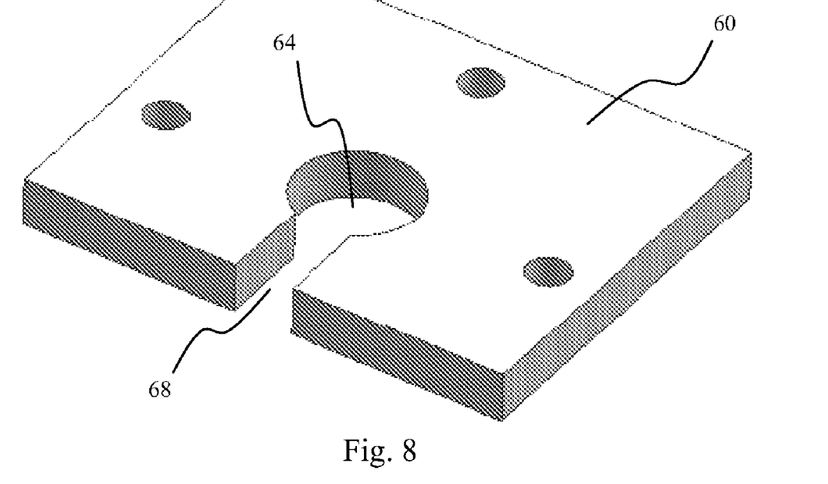
FIG. 8 shows a lid of the test equipment.

Referring to FIG. 8, in order to keep the striker 20 inside the frame 30 a lid 60 of steel with a layer 62 of damping material of rubber arranged on the side facing the frame of the lid is provided. In the middle of the lid 60, a hole 64 may be provided for the striker's top. In an embodiment the lid 60 is made wider for one extra support 63 (shown i.a. in FIG. 5) arranged underneath the lid 60 and an extra screw hole is provided. A slot 68 is arranged from the middle and out to one of the long sides shown in FIG. 8, in order to have room for the release arm 84 which will run along one of the sides on the frame 30 up to the top.

Spring Tighter

Figure 9:
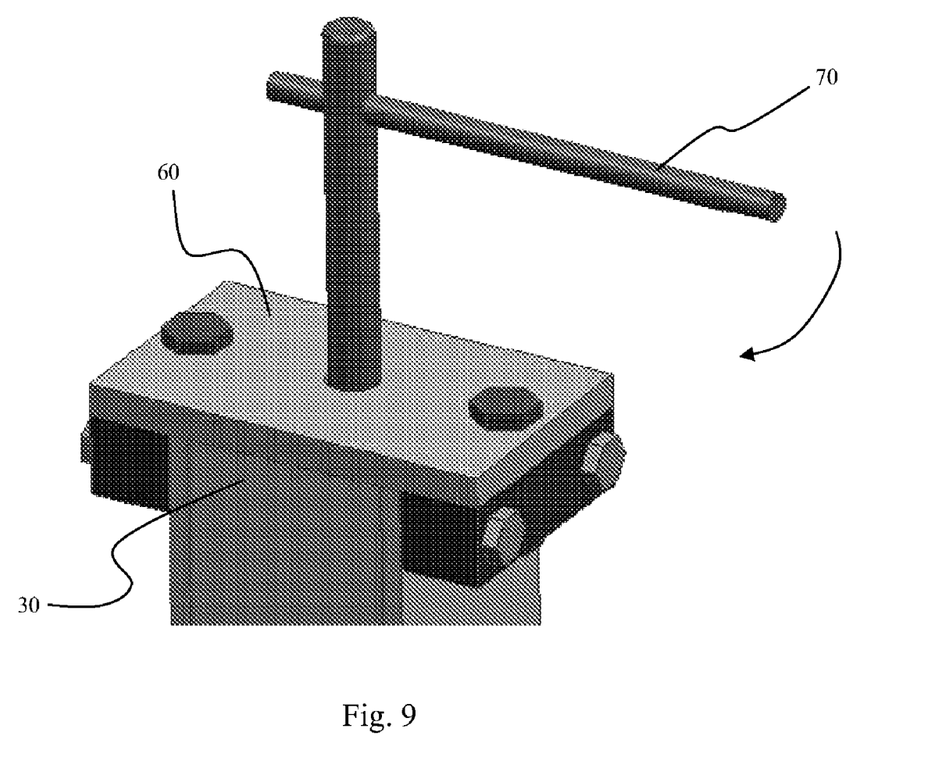
FIG. 9 shows a tightening arrangement of an embodiment of the test equipment.

The pressure spring 10 has to be loaded by compressing the spring. Depending on how much spring force that will be utilized, the spring has to be loaded differently. Different solutions of loading the spring 10 manually exists, one solution is illustrated in FIG. 9 wherein an arm 70 of lever which is threaded is used. This solution requires less manual power to force the spring down. When the winch 70 is turned, as illustrated by the arrow in FIG. 9, it is necessary to have a lid 60 that forces the winch 70 in right position and does not let it go up. The lid 60 has a threaded hole 64 in the middle for the winch 70 and two more holes to fasten the lid to the frame. The force may also be provided by a machine such as a drilling machine or the like.

In a different embodiment as shown in FIGS. 12 and 13 the spring tighter is a pneumatic arrangement using a standard cylinder named DNC-50-250-PPV-A 92. The diameter is 50 mm, the stroke 250 mm, the theoretical force at 6 bars return stroke is 990 N. This cylinder was chosen from the spring length 240 mm. The piston diameter 50 mm was calculated from the known spring force F and the known normal air pressure p of 6 bar, normally used in the industry today.

In FIG. 12 a guide is used, FENG-50-250 90 to fasten the cylinder to the frame 30. It looks like an H and gives stability both to the frame and to the cylinder.

Release Function

In order to keep the force element in an energised state, that is compressed, the equipment comprises securing arrangement able to release the energy maintained in the force element.

In an embodiment of the invention the test equipment comprises two cotters (not shown), however, it should be noted that one or more cotters could be used. The benefit with two cotters, one at opposite side, is that the striker is released from two points which gives a linear release. The difficulty is to get both cutters released at the exact same time. Using only one cutter makes it is easier to design the test equipment. By making the striker long enough the equipment avoids that the striker could be released in a slanting angle and get stuck on the way up.

In the illustrated embodiment in FIGS. 6a-6b the holes 35 in the frame 30 are made for the cotter to slide through and in that way release/lock the spring 10. The holes 35 are big enough to handle the pressure that arises on the face inside the hole 35. The holes 35 may be in any shape. However, in the illustrated embodiment the holes 35 are of circular shape which facilitates the manufacturing of the equipment. Using circular holes 35 will work well regarding bearing value and bending. The force that is required to take out the cotter from the hole is the friction between the cotter and the striker, which depends on the spring force.

It should be understood that other designs of release mechanisms may be used, such as, wires (plastic, metal) or the like.

In an alternative embodiment the release arrangement is a pneumatic arrangement as shown in FIGS. 12 and 13. The pneumatics is controlled by a control unit and attached to central source of pressurized compressed air. To release the spring a compact cylinder, ADVU-63-50-P-A 86, will be used shown in FIG. 12. Since it is necessary with a quick motion to release the spring a larger cylinder diameter is provided, 63 mm. The ADVU cylinder is exposed to the same spring force as the DNC cylinder 92. At the end of the piston 85 a release arm 84 is attached to slide in and out from the frame 30. The ADVU cylinder does not have a guide, but may be provided with one. The force from the spring 20 is vertical to a piston 85 and would break it without support. A house 82 is designed to guide the release arm 84 and slide bearings are placed inside. To fix the two cylinders together at the right position two mounting plates 88 are designed with attachment holes. One is placed on the DNC cylinder 92 and the other one standing behind the ADVU cylinder 86. To attach the frame 30 to the pneumatic system and to get stability in the complete design, two sorts of flanges 94 are designed shown in FIGS. 12,13.

In the illustrated embodiment of FIG. 12 the pneumatic releasing arrangement is combined with pneumatic tightening arrangement. However, it should be understood that is may also be combined with different tightening process, just as, the pneumatic tightening may be arranged with a different release mechanism.

Other types of assisted release systems such as hydraulic systems or the like may also be used.

Component Support 50

Figure 10:
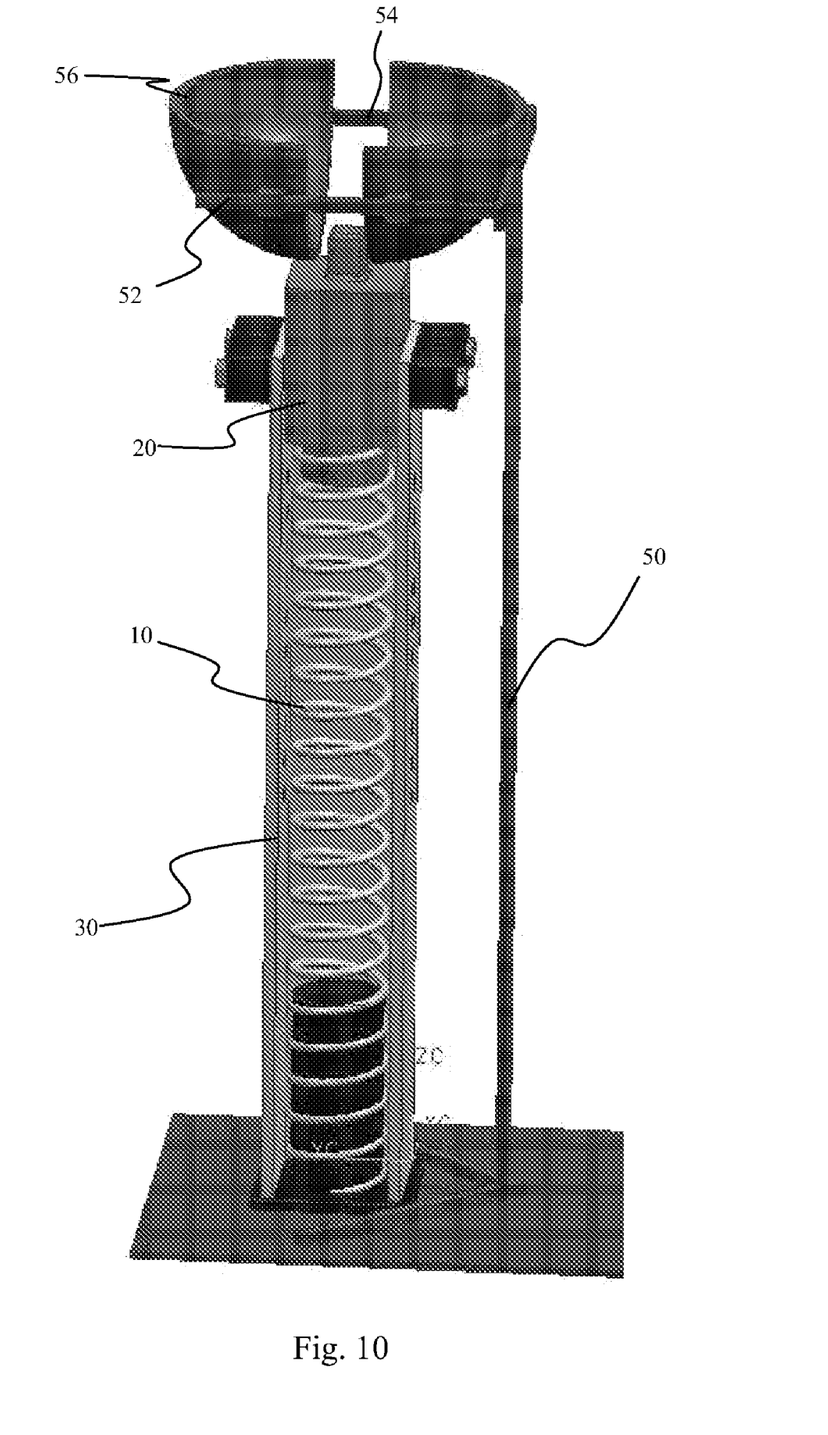
FIG. 10 shows an embodiment of a test equipment with a component support.

An embodiment of the test equipment comprises a circular adjustable component support 56 with an opening in the bottom for the striker to hit the component, as shown in FIG. 10. The circular support 56 may be arranged with a soft coating inside which facilitates the possibility to place the component on different edges, faces and corners depending on which test case that is performed. That is, the component may be set in different orientations in order to let the striker impact against the component at a certain area of the component.

In the illustrated embodiment the component support is hanging from a stand 50 with two movable "arms" 52, 54 which are adjustable. The adjustable component support can be moved laterally for different component sizes. The chosen material for the component support may be a funnel made in plastic which is cut/saw in half in the middle and secured to a thin metal wire.

In an alternative embodiment the component support consists of an arm 50 and a clip 58, shown in FIG. 11. The arm is adjustable in all three dimensions. The clip 58 holds the component in it is desired position; the aim is that the clamp force should be as small as possible so that it does not affect the component when it is hit by the striker. By inserting an extra spring the clamp force may be reduced.

In a pneumatic embodiment, shown in FIGS. 12 and 13, the force of the force element is set by an adjustable sensor of the vertical pneumatic cylinder.

Further Details of Different Embodiments of the Invention

In order to make the design safer, a box of Plexiglas may be placed around the equipment as a housing.

In an alternative embodiment ball bearings or roller bearings may be used to guide the striker inside the frame.

The Component Impact Tester showed the same result as the Free Fall test on two different materials. A material of bad plastic did not pass the component tester when it was hit with velocities between 15-20 m/s, but it passed when the velocity was lower then 15 m/s. The same tests were made on a material of good plastic as well, it passed all stages in the Component Impact Tester, just as in the free fall test.

The embodiment of using a basic pneumatic solution to tighten and release the spring works well. The manual work to use the equipment is reduced to a minimum. To make the design even safer, there are possibilities to make changes in the connections between the cylinders in the pneumatic system. One should try and reduce the risk to press operation buttons in wrong order, which would lead to damage both to the equipment and in worst case even to the user. The safety is important to consider because it is one of the basic aims that the equipment needs to fulfill.

Furthermore, to make the component support 50 more functional to use, it may be a size bigger and have lower clamping force so it affects the component as little as possible and is able to grab around large edges. The support may be placed further away from the hole, which would make it easier to rig the component into the right position. The test equipment has the possibility to point out weaknesses in the plastic material and the same results are given by the Free Fall test.

Conclusively, time to rig the component and to perform one test sequence in an embodiment of the test equipment has been measured to 60 seconds in average. Time to rig the component depends on the user, an experienced user requires less time to rig then an unpractised. It is easy to use the test equipment. The test instructions are illustrated with pictures and they are easy to understand for an average English speaking person. The repeatability are good. The responsibility to rig the component lies on the user and the repeatability can be compared to Free Fall. The test equipment is experienced safe. The result is easy to identify; visible cracks or not. The size of the test equipment is satisfactory. The mass of the components that are embraced of the test is in a large interval. It is possible to rig the component, vertically, lateral and in different angles. The equipment is experience robust which is satisfying. The results are based on the measurements with the high-speed camera. Total mass of the equipment is 20 kg. It is easy to change worn out parts of the equipment.

Figure 14:
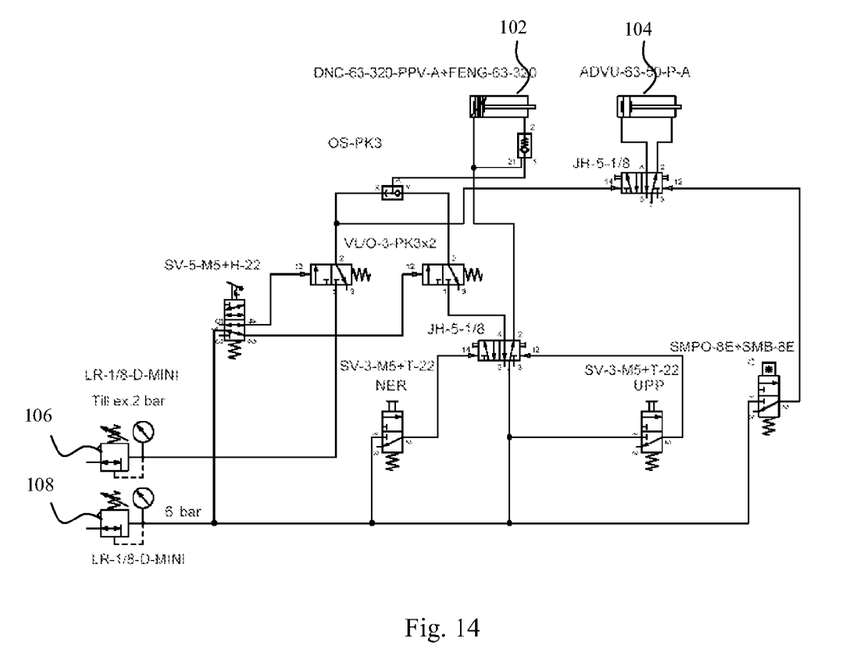
FIG. 14 shows a connection diagram of the pneumatics.

The Component Impact Test method fulfills an important need, which is, that the test result on one component should correlate or be able to be compared with the same result in a Free Fall test on the same phone. As a proof of this is the good plastic component which did not brake even with the highest velocity. This means that a specific value could not be determined. If the range of velocities is increased a more specific valuation of what the component can or can not handle may be determined Operation of the Equipment In FIG. 14 a connection diagram of the pneumatic solution of FIGS. 12 and 13 is shown. The vertical pneumatic cylinder 92 in FIG. 12 is illustrated as a cylinder denoted as 102 and the horizontal pneumatic cylinder arrangement 86 in FIG. 12 is illustrated as a cylinder denoted as 104. The different compressed air sources are denoted as 106 being the source of the lower pressure, in the illustrated embodiment 2 bar, and 108 being the source of the higher pressure, in the illustrated example 6 bar. As disclosed in FIG. 14 higher pressure may be used to lower the vertical cylinder in order to overcome the force of the force element 10 and to withdraw the release arm 84 by pushing the horizontal cylinder to its lower position.

Figure 15:
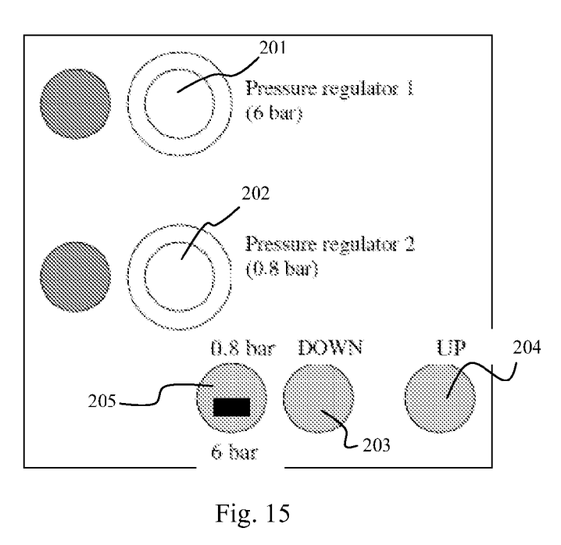
FIG. 15 shows a user interface of an operation box of an embodiment of the test equipment.

When operating the equipment in the pneumatic embodiment the operator controls the process by using buttons. An embodiment of the user interface is shown in FIG. 15. The pneumatic design may be made easier for the user. There should be no uncertainty of which button to press and in which order, an example of using the interface is disclosed below. Instead of having three buttons to control, it could be reduced to two. One button to lower the striker just under the lid during rigging the component, and another one to lower the striker completely, release it and finally raise it up to start position. To have fully control over the sequence, the only possible way should be to press the buttons in right order and not the other way around so something uncontrolled could happen.

In order to install the equipment the test equipment may be placed on a flat surface, close to a compressed-air supply. The ground should be steady for the equipment; it has to handle at least 20 kg. The equipment is placed so the tubing of the compressed air has free space and that there is nothing they can get entangled in. The large movable cylinder should have enough space in both positions, in low level and in high level. A maneuver box is placed in a position so all tubing have free outlets for the air.

An Embodiment to Operate the Equipment May be as Follows Referring to FIGS. 12, 13, and 15

Turn on the equipment by turning the compressed-air valve to a first position, the system is filled with air. The equipment is in a first state. Make sure that the small cylinder 86 is in its lowest position. An UP-button 203 is pressed and a second state will be reached. Verify that a component to be tested has faultless surfaces. Adjust a sensor on the pneumatic cylinder 92 to an eligible height resulting in a wanted force of impact/velocity of the striker element. Turn a switch 205 to a predetermined pressure and the small cylinder 86 is in high level engaging the striker element, a third state. Press DOWN-button 204. Check that the striker 20 descend under the lid 60, a fourth state. Place the component 40 according to a chosen scenario, that is, where should the striker impact the component. Make sure that the component 40 is placed just above the lid, 0-10 mm. A safety net may be used and may be placed around the test equipment. Turn the switch 205 to a second predetermined higher pressure, the striker 20 will descend until it reaches the sensor and the release arm 84 will then directly liberate the striker 20. The striker then impacts against the component at the selected velocity. Thereafter the component 40 should be inspected for defects.

The aim of the test is to find out how durable the component is. Start at a high value on the sensor and increase gradually. If the component has any faults, take a new one (from the same batch) and increase the value for sensor. Repeat procedure. If the component did not have any defects, observe the value that indicates the position of the sensor and check if it is acceptable for that special component and drop scenario. Turn off the equipment as well as the compressed-air valve when all tests have been performed. The system will be emptied of air and the equipment will return to the first state. The pressure of the system will be indicated by the indicating lights 201,202.

Figure 16:
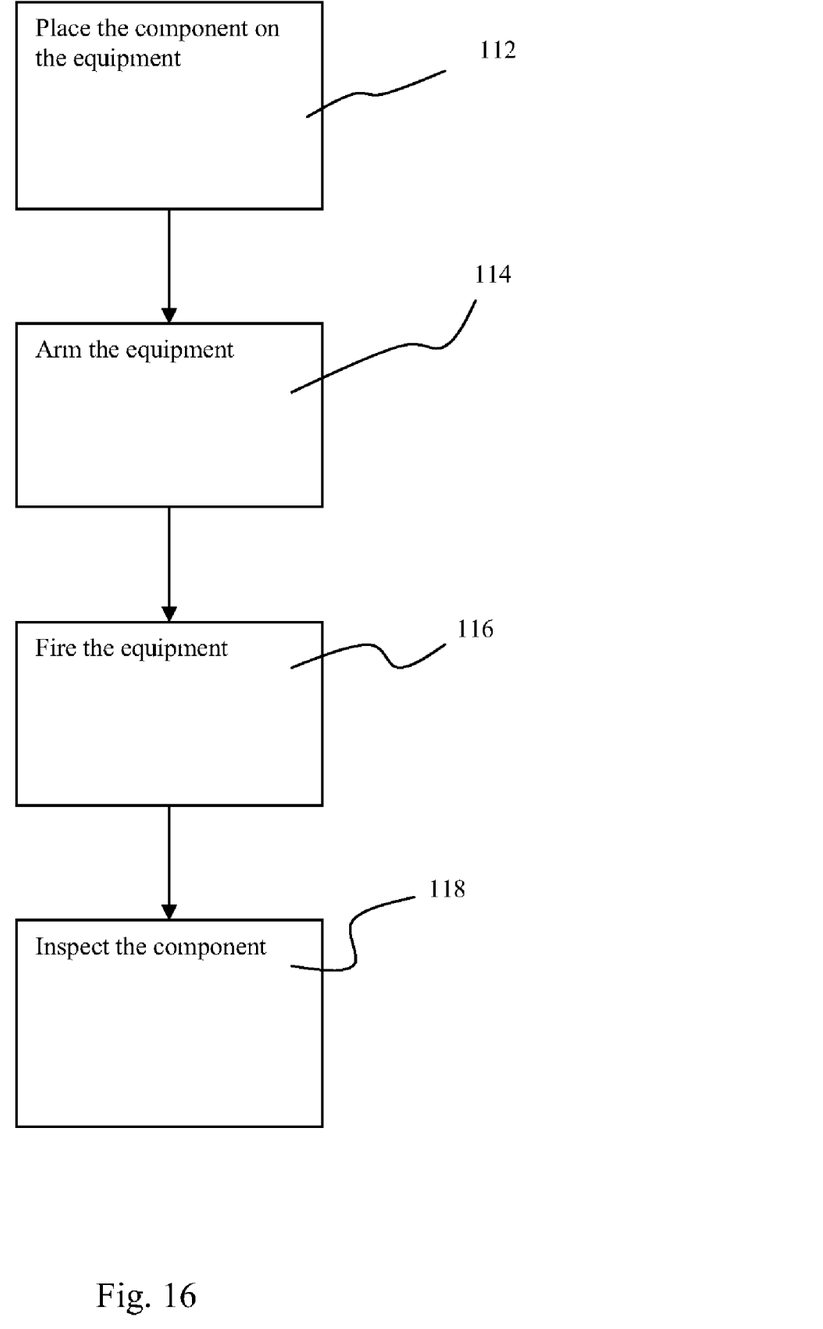
FIG. 16 shows a schematic overview of a method using an embodiment of the test equipment.

Referring to FIG. 16 a simplified block diagram of a method of using an embodiment of the test equipment is shown. In step 112, a component to be tested is placed in a component support arrangement. In step 114, the test equipment is armed, that is, the force element is placed in an energised state. By indication of the operator, such as a pressing of a button, the force element is released or as stated in step 116, the equipment is fired. When the component has been hit by the striker the component is inspected as stated in step 118. It should here be noted that the arming of the equipment may occur before the placing of the component, however, the safety of the operator is enhanced when the arming is done after the placing of the component.

Figure 17:
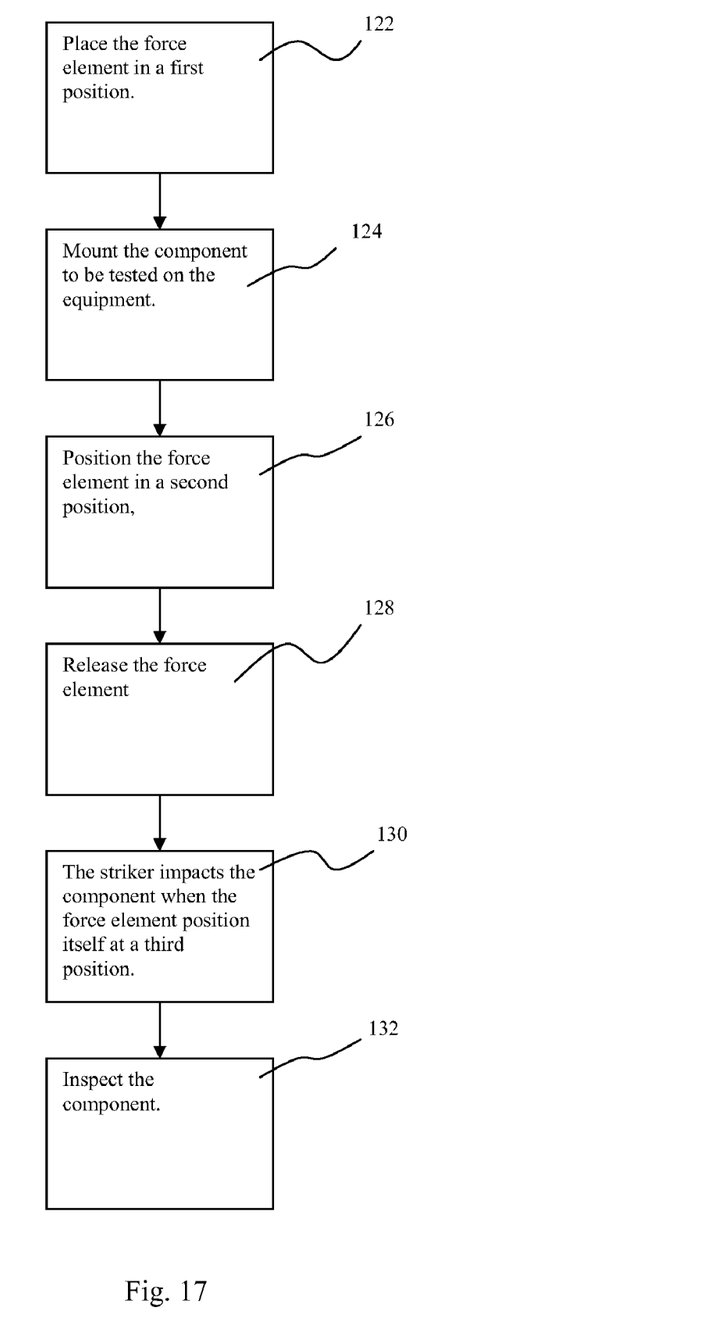
FIG. 17 shows a schematic block diagram of a method using an embodiment of a test equipment.

In FIG. 17 a block diagram of a method of using a pneumatic test equipment system of FIGS. 12-13 is shown. First the pneumatic cylinder 92 is moved to a top position and the release arm 84 is arranged to engage the striker 20.

In step 122, the vertical moving cylinder 92 moves the striker 20 to a first position, being a position placing the striker 20 just beneath the lid 60 but in a safe manner, that is, if accidentally released from the first position the force of the spring 10 will be very low.

In step 124, a component 40 to be tested is mounted in the component support 50, for example, by clamping the component in a clip and orientating the component in a selected orientation in order to impact the component on a selected spot.

In step 126, the vertically moving cylinder 92 in connection with the release arm 84 is forcing the striker element 20 and force element 10 down to a second position. The second position being the position wherein the force element 10 is in an energised state, that is, the equipment is armed. The position is selected in order to generate a certain velocity of the striker 20 on impact.

In step 128, the horizontal moving release arm 84 is withdrawn from the striker element 20, thereby releasing the force element 10 and the striker 20.

In step 130, the striker 20 impacts the component 40.

In step 132, an operator of the test equipment or another person or equipment inspects the component 40 to see if any cracks or the like may have occurred. The information from the inspection may then be used to determine characteristics of the component, for example, by repeating the process with different applied forces on the force element, that is, the distance the force element is lowered. The information may be used as a representation of characteristics of the component.

The method is used to compensate the weight difference of the component and the complete article, that is, the article with all its components mounted therein.

It will be appreciated that control of the test apparatus may be a programmable digital computer, a special computer, an asic (application specific integrated circuit) or some other control device.

The invention claimed is:

1. A test equipment system for testing a component of an article comprising:
    a force element arranged to move from a first position to a second position,
    a striker element connected to the force element arranged at one end of the force element,
    a frame structure arranged to guide and support the force element between the two positions, the second end of the force element being connected to the frame structure,
    wherein the force element in the first position is in an energised state and the force element in the second position is arranged to impact the striker element against the component, and
    wherein the test equipment system comprises a locking arrangement arranged to maintain the force element in the first position where the force element is in an energised state and wherein the locking arrangement is arranged to release the energy in the force element on command from a controller, and
    wherein the locking arrangement is a pneumatic arrangement comprising a compressed air source, a horizontal moving piston arranged to move perpendicular to the force direction of the force element and controlled by the compressed air source, a release arm connected to the piston, and a guiding house arranged to guide the release arm into the frame structure.

2. A test equipment system according to claim 1, wherein the test equipment system further comprises a component support arranged to support the component in an optional orientation and to place the component so that the striker impacts the component when the force element is in the second position.

3. A test equipment system according to claim 1, wherein the force element is a spring element.

4. A test equipment system according to claim 1, wherein a lid is arranged at the top of the frame structure.

5. A test equipment system according to claim 1, wherein the equipment further comprises a tighter mechanism in order to position the force element in the first position.

6. A test equipment system according to claim 5, wherein the tighter arrangement is a screwing arrangement arranged to engage a lid arranged at the top of the frame and arranged to be tightened manually or by a machine.

7. A test equipment system according to claim 5, wherein the tighter arrangement is a pneumatic arrangement comprising a cylinder arranged to move in parallel to the force direction of the force element.

8. A method of testing a component of an article by using a test equipment system comprising a force element, a striker element connected to an end of the force element, a frame structure, and the second end of the force element is secured to the frame structure, comprising the steps of:
    moving the force element to a first position wherein the force element is energised;
    releasing the energy in the force element, and thereby impacting the striker element against the component, and
    wherein the test equipment further comprises a pneumatic arrangement comprising an compressed air source, a piston arranged to move perpendicular to the force direction of the force element and controlled by the compressed air source, a release arm connected to the piston, and a guiding house arranged to guide the release arm into the frame structure and a cylinder arranged to move parallel to the force direction of the force element, and wherein the method further comprises the initial steps of:

positioning the force element in a third position lowering the striker element away from the component support just below a lid arranged at the frame structure; and mounting the component in a component support so that the striker element impacts the component at a selected area of the component.

9. A method according to the claim 8, wherein the method further comprises the step of:

mounting the component in a component support so that the striker element impacts the component at a selected area of the component.

10. A method according to claim 8, wherein the step of moving the force element is performed by the release arm engaging the striker element and the cylinder forcing the force element to the selected first position by using compressed air from the compressed air source.

11. A method according to claim 10, wherein the step of releasing the energy is performed by withdrawing the release arm from the striker element using compressed air from the compressed air source.

12. A method according to the claim 11, wherein the method is controlled by an operator using buttons.

13. A method according to claim 8, wherein the method comprises the step of selecting a force of the force element for compensating the weight difference between an assembled article and the component.

14. A method according to claim 8, wherein the method further comprises the steps of:

inspecting the component after the component has been impacted by the striker element; and determining characteristics of the component by using information from the step of inspecting.

* * * * *